United States Patent [19]

Hyland et al.

[11] Patent Number: 4,997,816

[45] Date of Patent: Mar. 5, 1991

[54] INDUCTION OF FERTILE OVULATION IN ANOESTROUS MARES

[75] Inventors: John H. Hyland, Sandringham; Leo B. Jeffcott, Werribee, both of Australia

[73] Assignee: The University of Melbourne, Australia

[21] Appl. No.: 358,479

[22] Filed: May 30, 1989

Related U.S. Application Data

[63] Continuation of Ser. No. 225,571, Jul. 26, 1988, abandoned, which is a continuation of Ser. No. 862,295, May 12, 1986, abandoned.

[30] Foreign Application Priority Data

May 10, 1985 [AU] Australia .................... PH00518

[51] Int. Cl.$^5$ ................ A61K 37/38; A61K 37/24
[52] U.S. Cl. ................ 514/12; 119/174; 514/8; 514/13; 514/14; 514/15; 514/21
[58] Field of Search ................ 514/8, 12–15, 514/21; 119/1

[56] References Cited

PUBLICATIONS

Arthur, G. H. et al., *Veterinary Reproduction and Obsterics (Theriogenology)*, Sixth Edition, Bailliere Tindall, London, pp. 9–10.
Vandeplassche, M., 1985 "Comparative" Aspects of the Postpartum Period in Domestic Animals," *Endocrine Causes of Seasonal and Lactational Anestrus in Farm Animals*", Martinus Nijhoff Publishers, pp. 186–188.
*Chem. Abst.*, 83,72 (1975), Abst. No. 22768x.
Chakraborty, *Journal of Animal Science*, 39, No. 6, 1150–1157 (1974).
Nett, *Biology of Reproduction*, 24, 1145–1155 (1981).
McLeod, *J. J. Reprod. Fert.*, 65, 223–230 (1982).
Ginther, O. J. *Reproductive Biology of the Mares*, Basic and applied Aspects, Equiservices, WI (1979), pp. 125–132.
Allen, *Equine Vet. J.*, 12 (1), 27–28 (1980).
Hennington, *Theriogenology*, Technical Article 17290 Texas Agr. Exp. Sta. 1982.
Mastronardi, *Acta Med. Vet.*, 30, 259–264 (1984).
Chem. Abstr. vol. 83 (1975) 22768.
Chem. Abstr. vol. 91 (1979) 50044.

*Primary Examiner*—Ronald W. Griffin
*Attorney, Agent, or Firm*—Andrus, Sceales, Starke & Sawall

[57] ABSTRACT

The present invention is directed to a method for inducing or stimulating, in anovulatory mares, the onset of fertile ovulation by administering, to an anovulatory mare, a gonadotrophin or gonatrophin-releasing substance at a rate with respect to time that maintains a substantially continuously present concentration of the substance in the mare sufficient to initiate an induced fertile ovulation.

7 Claims, No Drawings

INDUCTION OF FERTILE OVULATION IN ANOESTROUS MARES

CROSS REFERENCE TO RELATED APPLICATIONS

The present application is a continuation of U.S. patent application Ser. No. 07/225,571, filed July 26, 1988, now abandoned, which in turn is a continuation of U.S. patent application Ser. No. 06/862,295, filed May 12, 1986, now abandoned.

The mare has a well-defined physiological breeding season which is cued to increasing daylength and extends from approximately October to February in south-eastern Australia. Regulatory authorities have imposed a birth date of Aug. 1 on horses in the southern hemisphere and, because the mare has an 11-month gestation period, breeding must commence early in September for foals to be born close after Aug. 1 of the following year. It is desirable to have foals born close to the Aug. 1 deadline because these animals have growth advantages and potential performance advantages over later-born foals. The problem for the horse breeding industry is that during early September only 20% of mares are undergoing regular ovulatory oestrous cycles in southern Australia. Any method which will tend to induce ovulation during this time will therefore be of benefit to the horse breeding industry by making more efficient use of stallions and by enabling mares to be bred so that foals are born close to Aug. 1st.

In the northern hemisphere the equivalent date is Jan. 1.

The present invention provides a method of inducing ovulation in mares comprising administering to a mare an ovulation inducing amount of a gonadotrophin releasing material over a period of at least seven days.

Said period may be extended as desired or necessary and 14–28 days will generally be preferred and effective to induce ovulation.

Preferably said material is administered to the mare at intervals of not greater than one day, preferably at intervals of not greater than one hour and more preferably substantially continuously during said period.

To induce ovulation at an appropriate time, it is preferred that, relative to the proposed "birthday," treatment with GnRH should commence between 25 and 76 days, more preferably 25 and 61 days and most preferably 25 and 46 days after the "birthday" in any one year.

It is to be noted that the above dates and times presume a normal or average gestation period.

As said material there may be used a naturally occurring gonadotrophin releasing hormone (GnRH) or a synthetic GnRH, luteinizing hormone (LH) human chorionic gondatrophin (hCG) follicle stimulating hormone (FSH) and analogues of such.

A dosage rate equivalent to from 25–100 ng/kg/hr will normally suffice but may be varied dependent on the effectiveness of said material.

Any suitable mode of administration may be adopted but in general a mode of administration which approaches substantially continuous administration during said period will be preferred.

Suitable modes of administration include use of osmotic pumps, subcutaneous infusion, solid implants, intravaginal implants and subcutaneous injection at intervals. In general, oral administration is not suitable as said material will usually be broken down by stomach acids and digestive enzymes. However, oral administration in a form avoiding such break down will be suitable.

Accordingly, the present invention also provides a pharmaceutical vehicle adapted to be associated with the body of a mare and adapted to administer an ovulation inducing amount of a gonadotrophin releasing material over a period of at least seven days.

The following Examples illustrate the present invention.

EXAMPLES

Drugs and equipment

Synthetic gonadotrophin releasing hormone (GnRH; pGlu-His-Trp-Ser-Tyr-Gly-Leu-Arg-Pro-Gly-NH$_2$) was purchased from the United States Biochemical Corp., Cleveland, OH. This material is identical to naturally-occurring GnRH but is synthetically produced.

Delivery of GnRH was achieved via osmotic minipumps (OMP; Alza Corp., Palo Alto, CA:). These pumps are constructed of a rigid, semi-permeable membrane, inside which is suspended a water-proof bag which is filled with the substance to be infused. The neck of the bag is open to the atmosphere. Between the bag and the membrane a special osmotic solution is held. This solution causes an influx of water through the semi-permeable membrane when the OMP is placed in the body of animals. The influx of water collapses the bag at a fixed rate and the substance contained in the bag is expelled from the OMP at a steady rate. The model of OMP used for this experiment had an infusion rate of approximately 2.86 $\mu$l/hr for 28 days.

EXAMPLE I

Fourteen Standardbred mares in deep anoestrus were divided into 3 groups. Group C (controls; n=5) received no treatment while Group 50 (n=5) and Group 100 (n=4) were given infusions of GnRH at rates of 50 ng/kg/h and 100 ng/kg/h respectively. The GnRH was administered via subcutaneously implanted osmotic minipumps (OMP) for 28 days. Blood samples were collected daily and ovarian palpation and oestrus detection was carried out 3 times per week or daily if a follicle >3.5 cm was detected.

Results

Ovulation occurred in none of the control mares, 2 of 5 Group 50 mares and 3 of 4 Group 100 mares. Average time from OMP insertion to ovulation was 18.5 days for Group 50 and 17.3 days for Group 100.

Results of hormone analysis showed:
(a) Surges of LH were associated with ovulation in each case.
(b) Mean daily plasma LH concentrations were higher in both treated groups compared to control mares.
(c) Plasma GnRH concentrations increased in treated groups until Day 12 of the experiment and declined slowly thereafter.
(d) There was an increase in LH pulse frequency in all groups during the period of the experiment. However, LH pulse frequency was significantly ($p<0.05$) higher in both treated groups compared to the controls within 7 days of insertion of OMP. By Day 21 of the experiment, Group 100 mean LH pulse frequency was significantly ($<0.05$) higher than that of the controls. By Day 28 there was no difference in LH pulse frequency between the groups.

(a) There was no statistical difference in LH pulse amplitude between the 3 groups on any of the days studied.

EXAMPLE II

Animals

Ten young Standardbred mares of 3 to 5 years of age as judged by wear of the teeth were used in the experiment. During the experiment, the mares were fed hay twice daily and kept in a paddock. The mares were vaccinated against Tetanus and Strangles and were given regular anthelmintic and lice treatments. Their body condition during the experiment was good to very good.

Ovarian palpations were carried out and blood was collected from the mares every 2 or 3 days for 4 weeks prior to commencement of the experiment. These examinations revealed that the ovaries contained follicles 2-3 cm in diameter and that plasma progesterone concentrations were very low for at least 4 weeks before the experiment. These observations indicated that the mares were in transitional or "shallow" onoestrus prior to the experiment.

Experiment procedure

The experiment commenced on Sept. 10, 1984. Mares were randomised in pairs to a Treated group or a Control group until all the mares had been assigned to groups by Sept. 21. The mares were paired on the basis of each mare having approximately equal ovarian follicular activity. Each treated mare was weighted just prior to the experiment. The dose of GnRH (100 ng/kg/hr) to be administered over 28 days was calculated and dissolved in sterile, physiological (0.9%) saline. The solution was loaded into an OMP and placed in a beaker of saline at room temperature overnight to allow for the "start up time" of the OMP.

The OMP were inserted subcutaneously in the side of the necks of the treated mares, under local infiltration anaesthesia. The pumps were retained using 1 or 2 mattress sutures in the skin.

After insertion of the OMP, the treated and control mares were run as a group in a single paddock. Every 2 or 3 days the mares were brought into the yards. Ovarian palpations were carried out and blood samples were collected on these days. In addition, the mares were teased with a vigorous stallion, to detect oestrus. Mares which showed oestrus were bred to the stallion every other day until ovulation had been detected by ovarian palpation.

Blood samples were assayed for lutsinizing hormone (LH) and progesterone concentrations.

Ultrasound echography was used to diagnose pregnancy 14 days after ovulation. Subsequent ultrasound examinations were made every 2 or 3 days until Day 45 of pregnancy, when the experiment was terminated.

Results

Four of 5 treated mares and 1 of 5 control mares ovulated during GnRH infusion. Time of ovulation ($\bar{x} \pm$ s.e.m.) from commencement of the experiment was $18.6 \pm 4.1$ days for treated mares and $54.8 \pm 10.8$ days for control mares. These differences were highly significant ($p<0.01$), measured by Student's "t" test.

Four of 5 treated mares conceived in association with the first ovulation after insertion of the OMP. Mean ($\bar{x} \pm$ s.e.m.) day of conception was $26.6 \pm 9.7$ and $67.8 \pm 16.0$ for treated and control mares, respectively. This difference was highly significant ($p<0.01$) when measured by student's "t" test.

Conceptus and embryo growth rates in both groups of mares were normal as judged by ultrasound measurements.

Results of hormone essays showed that LH surges were associated with ovulation in all the mares. Furthermore, within 2 or 3 days of OMP insertion in treated mares, there was a rapid increase in plasma LH concentrations. In 3 treated mares the initial rise in plasma LH concentrations was maintained for 10, 13 and 18 days and was associated with ovulation. In the remaining 2 treated mares the initial LH rise lasted 7 and 12 days respectively and was not associated with ovulation. It was followed by a second period of elevated plasma LH concentrations which were associated with ovulation. Plasma LH concentrations in control mares remained <1 ng/ml after assignment to the experiment until several days prior to ovulation, when plasma LH concentrations rose rapidly over several days and were associated with ovulation.

Plasma progesterone concentrations in both groups of mares rose after ovulation to reach concentrations consistent with the presence of a functional corpus luteum eon one of the ovaries.

Discussion

The results strongly suggest that subcutaneous infusion of GnRH at a rate of 100 ng/kg/hr to mares during transitional seasonal anoestrus results in fertile ovulation. The reasons are as follows (1) Four of the 5 treated mares ovulated during the 28 day period of the infusion. The remaining treated mare responded to GnRH infusion within 2 days of OMP insertion with a rapid increase in plasma LH concentrations, but this was not associated with ovulation.

(2) The average time of ovulation from the commencement of the experiment was significantly ($p<0.01$) shorter in the treated mares (18.6 days) then the control mares (54.8 days).

(3) Four of the 5 treated mares became pregnant to the induced ovulation and the average day of conception for the group was 26.6 days after OMP insertion proving that the first ovulation after OMP insertion was fertile. As far as could be ascertained by ultrasound examination, growth of the conceptus was normal in the treated mares.

(4) After insertion of OMP, plasma LH concentrations rose rapidly within 2 or 3 days in all treated mares. This initial rise was augmented by an apparent endogenous surge release of LH in 3 of the mares, which was associated with ovulation. In the other 2 treated mares the initial increase of plasma LH was not associated with ovulation. In these mares, ovulation occurred 15 and 33 days respectively after insertion of the OMP, suggesting that GnRH infusion stimulated LH synthesis and release by the pituitary gland.

Length of administration

The period of GnRH infusion in this Example was for 28 days. As 3 of 5 treated mares ovulated 10, 13 and 15 days after insertion of OMP, it is probable that the period of infusion can be reduced from 28 days in certain mares with 7 days being a probable lower limit.

EXAMPLE III

Animals

Sixteen maiden Standardbred mares, 3 to 6 years of age were used in the experiment which was conducted during deep winter anoestrus in 1985. The mares were in good to excellent condition and were run in 2 outside paddocks during the period of the experiment.

Experimental procedure

The mares were divided into 3 groups. Group C (n=5) were untreated and acted as a control group, while Group 50 (n=5) and Group 100 (n=6) received infusions of GnRH at rates of 50 ng/kg/h and 100 ng/kg/h, respectively. The GnRH was delivered via subcutaneously implanted OMP for 28 days, starting on July 2, 1985. Ovarian palpations and oestrus detection was carried out 3 times per week or daily when an ovarian follice of >3 cm diameter was detected.

Results

Ovulation occurred in none of the control mares, 1 of 5 group 50 mares and 4 of 6 Group 100 mares. Average times from OMP insertion to ovulation was 24 days for Group 50 and 21.8 days for Group 100.

EXAMPLE IV

Animals

Seventeen Standardbred and Standardbred-type mares 3 to 9 years of age were used in the experiment, which commenced on Oct. 2, 1985, when the mares were in transitional anoestrus.

Experimental procedure

The mares were divided into 2 groups. One group (n=g) was treated with an infusion of GnRH at a rate of 100 ng/kg/h delivered by subcutaneously implanted OMP for 28 days. The mares were run in paddocks during the experiment and brought into yards every 2 or 3 days, during which time oestrus detection was carried out. Mares were bred to a stallion every other day they showed oestrus, until ovulation had been detected by ovarian palpation. Blood samples were collected 3 times per week for determination of plasma LH and progesterone concentrations. Ultrasound echography was used to diagnose pregnancy 14 days after ovulation, and every 2 or 3 days thereafter until Day 45 of pregnancy, when the experiment was terminated.

Results

Eight of 9 treated mares and 2 of 8 controls ovulated during the period the OMP were functional. The average time of ovulation ($\bar{x}\pm$s.e.m.) from commencement of the experiment was 33.9±4.2 days for the controls and 18.8±4.3 days for the treated mares. This difference was significant (P<0.05) when measured by Student's "t" test.

The average day of conception ($\bar{x}\pm$s.e.m.) from commencement of the experiment was 35.7±6.6 days and 24.4±8.1 days for the control and treated mares, respectively. The difference was significant when measured by Student's "t" test (P<0.05). Ultrasound measurement of the developing embryos suggested that embryo growth rates were normal in both groups. One mare in each group failed to conceive.

Hormone assays indicated that LH surges were associated with ovulation and plasma progesterone profiles were consistent with the formation of a functional corpus luteum in all the mares.

| Combined results Deep anoestrus (Example I, 1984, Example II, 1985) | | | |
|---|---|---|---|
| Group | No. mares | Proportion mares Ovulating | Percentage mares Ovulating |
| Controls | | | |
| 1984 | 5 | 0/5 | 0 |
| 1985 | 5 | 0/5 | 0 |
| Combined | 10 | 0/10$^a$ | 0% |
| Group 50 (50 ng/kg/h) | | | |
| 1984 | 5 | 2/5 | 40 |
| 1985 | 5 | 1/5 | 20 |
| Combined | 10 | 3/10$^{ab}$ | 30% |
| Group 100 (100 ng/kg/h) | | | |
| 1984 | 4 | 3/4 | 75 |
| 1985 | 6 | 4/6 | 67 |
| Combined | 10 | 7/10$^b$ | 70% |

$^{a, b}$P < .01 Chi Square Test

| Transitional anoestrus (Example II, 1984, Example IV, 1985) | | | |
|---|---|---|---|
| Group | No. mares | Day of ovulation ($\bar{x}\pm$ s.e.m.) | Day of conception ($\bar{x}\pm$ s.e.m.) |
| Controls | | | |
| 1984 | 5 | 54.8 ± 10.8 | 67.8 ± 16.0 |
| 1985 | 8 | 33.9 ± 4.2 | 35.7 ± 6.6$^+$ |
| Combined | 13 | 41.9 ± 5.5 | 49.1 ± 8.7 |
| Treated (100 ng/kg/h GnRH) | | | |
| 1984 | 5 | 18.6 ± 4.1 | 26.6 ± 9.7 |
| 1985 | 9 | 18.6 ± 4.3 | 24.4 ± 8.1$^+$ |
| Combined | 14 | 18.6 ± 3.0*** | 25.2 ± 6.0* |

*P < .05,
***P < .001 compared to controls
$^+$One mare in each group failed to conceive The table shows that when the data for the 2 years are combined the average day of ovulation in the treated mares occurred approximately 23 days earlier than the controls. More importantly, however, the day of conception in the treated mares occurred 24 days earlier than the controls. It is likely that these differences will be increased if treatment is commenced early in September or early in February in the southern and northern hemispheres, respectively. In the experiments outlined above, the differences in the time to ovulation and conception between treated and control mares was greater in 1984, when treatment commenced on Sept. 10, than in 1985 when treatment did not commence until Oct. 2. Despite the later start in 1985, conception occurred 3 to 4 weeks earlier in the treated mares. As the breeding season is approximately 15 weeks in length, this saving is a considerable advantage. By judicious use of the treatment, studmasters would be able to eliminate some of the economic cost associated with the early breeding season.

If desired GnRH may be administered to mares after incorporation of the hormone into continuous release pharmaceutical compositions such as ICI 118630 as described in Australian Patent Specification No. AU-/A/79986/82. The entire contents of the provisional specification lodged with Australian patent application No. 00518 are hereby imported into this specification and form part of the disclosure of this specification.

The claims form part of the disclosure of this specification.

We claim:

1. A method of stimulating the onset of ovulation in anovulatory mares comprising:

administering, to an anovulatory mare, a gonadotrophin or gonadotrophin-releasing material at an administration rate equivalent to at least about 100 ng/kg/hr for a period of at least about fourteen days to maintain a substantially continuously present concentration of the material in the mare sufficient in magnitude to induce ovulation.

2. A method of claimed in claim 1 wherein said material is administered to the anovulatory mare at intervals of not greater than one hour.

3. A method as claimed in claim 1 wherein said material is administered to the anovulatory mare substantially continuously during said period.

4. A method as claimed in claims 1, 2, or 3 wherein said material is selected from naturally occurring gonadotrophin-releasing hormone (GnRH), synthetic GnRH, luteinizing hormone (LH), human chorionic gonadotrophin (HCG), follicle stimulating hormone (FSH) and analogs thereof.

5. A method as claimed in claims 1, 2, or 3 wherein said material is administered to the anovulatory mare at an administration rate equivalent to about 100 ng/kg/hr of GnRH and is administered over a period of approximately 14 to 28 days.

6. A method as claimed in claim 5 wherein said material is administered to the anovulatory mare over a period of about 28 days.

7. A method as claimed in claim 1, wherein said administration of said material commences between about 25 and 76 days after the previous official equine birthday in the geographical region where the horse is located.

* * * * *